United States Patent [19]

Brewster et al.

[11] Patent Number: 4,803,220

[45] Date of Patent: Feb. 7, 1989

[54] PHARMACEUTICAL AGENTS

[75] Inventors: Andrew G. Brewster, Bollington; George R. Brown, Wilmslow; Michael J. Smithers, Macclesfield, all of United Kingdom

[73] Assignee: Imperial Chemical Industries PLC, London, United Kingdom

[21] Appl. No.: 750,101

[22] Filed: Jun. 28, 1985

[30] Foreign Application Priority Data

Jul. 6, 1984 [GB] United Kingdom ............... 8417314

[51] Int. Cl.$^4$ ................... A61K 31/335; C07D 319/06
[52] U.S. Cl. .................................. 514/452; 549/375; 546/184; 544/109; 544/315; 544/191; 544/184; 544/231.2
[58] Field of Search ............... 549/375; 514/452, 184, 514/191, 227, 315; 556/170; 544/109; 546/184

[56] References Cited

U.S. PATENT DOCUMENTS 4,567,197 1/1986 Brewster et al. ................... 514/452

FOREIGN PATENT DOCUMENTS 94239 11/1983 European Pat. Off. ............ 549/375

Primary Examiner—Nicky Chan
Attorney, Agent, or Firm—Cushman, Darby & Cushman

[57] ABSTRACT

The invention concerns the novel racemic and la-evorotatory optically active forms of the thromboxane $A_2$ antagonist 5(Z)-7-[2,4,5-cis]-4-o-hydroxyphenyl-2-trifluoromethyl-1,3-dioxan-5-yl)heptenoic acid of formula I, their salts, pharmaceutical compositions, and processes for their manufacture and intermediates therefor. The pharmaceutical agents and their compositions are of value in certain pulmonary and/or vascular disorders.

7 Claims, No Drawings

PHARMACEUTICAL AGENTS

This invention concerns novel pharmaceutical agents; and, more particularly, novel 4-phenyl-2-trifluoromethyl-1,3-dioxan-5-ylheptenoic acid derivatives which antagonise one or more of the actions of thromboxane $A_2$ (hereafter referred to as "$TXA_2$") and which are of value as therapeutic agents.

It is known that $TXA_2$ is a potent aggregator of blood platelets and a powerful vasoconstrictor. $TXA_2$ is also a potent constrictor of bronchial and tracheal smooth muscle. $TXA_2$ may therefore be involved in a wide variety of disease conditions, for example ischaemic heart disease, such as myocardial infarction, angina, cerebrovascular disease such as transient cerebral ischaemia, migraine and stroke, peripheral vascular disease such as atherosclerosis, microangiopathy, hypertension and blood clotting defects due to lipid imbalance, and pulmonary disease such as pulmonary embolism, bronchial asthma, bronchitis, pneumonia, dyspnoea and emphysema. Accordingly, compounds which antagonise the actions of $TXA_2$ may be expected to have therapeutic value in the prevention or treatment of any one or more of the above mentioned diseases or any other disease conditions in which it is desirable to antagonise the actions of $TXA_2$.

It is also known from our European patent application, publication No. 94239, that 4-phenyl-1,3-dioxan-5-ylalkenoic acid derivatives of the formula Z, having cis relative stereochemistry at positions 4 and 5 of the dioxane ring and wherein Ra and Rb are variously hydrogen, alkyl, halogenoalkyl, alkenyl and optionally substituted aryl or arylalkyl, Rc is hydroxy, alkoxy or alkanesulphonamido, n is 1 or 2, A is ethylene or vinylene, Y is (2–5C)polymethylene optionally substituted by alkyl and benzene ring B bears one or two optional substituents, possess the property of antagonising one or more of the actions of $TXA_2$ (hereafter referred to as "$TXA_2$ antagonism"). We have now discovered and herein lies the basis of our invention that particularly useful $TXA_2$ antagonism is shown by a novel compound of formula Z in which Ra is trifluoromethyl, Rb is hydrogen, Rc is hydroxy, n is 1, A is cis-vinylene, Y is trimethylene and benzene ring B is o-hydroxyphenyl.

According to the invention there is provided the novel compound 5(Z)-7-([2,4,5-cis]-4-o-hydroxyphenyl-2-trifluoromethyl-1,3-dioxan-5-yl)heptenoic acid of formula I, in racemic or laevorotatory optically active form; or a salt thereof.

It is to be understood that by "laevorotatory optically active form" is meant the more potent optically active form of the formula I compound having a negative optical rotation measured at the sodium D line, using methanol as a solvent. In the chemical formulae attached hereto, the particular configuration shown does not necessarily correspond to the absolute configuration.

Particular suitable salts of the compound of formula I are, for example, salts with bases suitable for use in the manufacture, isolation or purification of said compound, or salts with bases affording physiologically acceptable cations suitable for pharmaceutical purposes. Examples of the former salts are lithium, sodium, calcium, barium, aluminium and ammonium salts and salts with organic bases such as piperidine or morpholine and optically active bases such as ephedrine and alpha-methylbenzylamine. The salt with piperidine is particularly useful for isolation and purification purposes. Examples of salts suitable for pharmaceutical purposes are alkali metal and alkaline earth metal salts (such as sodium, potassium, magnesium and calcium salts), ammonium salts and salts with various organic bases such as with morpholine, piperidine and triethanolamine.

The compound of formula I may be obtained by analogous procedures to any of those described in our European patent, publication No. 94239, and such procedures for the manufacture of the formula I compound in racemic or laevorotatory optically active form are provided as a further feature of the invention. Typical preferred procedures are as follows:

(a) deprotecting a phenol derivative of the formula II wherein Rd is a suitable phenol protecting group such as (1–6C)alkyl, (3–6C)alk-2-enyl, tri(1–4C)alkylsilyl, tetrahydropyran-2-yl, 1-aryl-(1–4C)alkyl, (1–6C)alkanoyl or aroyl, for example methyl, ethyl, t-butyl, allyl, trimethylsilyl, tetrahydropyran-2-yl, benzyl, 1-phenylethyl, formyl, acetyl or benzoyl.

The deprotection reaction conditions necessarily depend on the protecting group used. However, in general, conditions which are standard in the art for the removal of the same protecting group in chemically analogous compounds are used. Thus, for example, when Rd is (1–6C)alkyl (and especially methyl) the deprotection may be carried out, for example, by heating with sodium thioethoxide in a suitable solvent, such as N,N-dimethylformamide or 1,3-dimethyl-3,4,5,6-tetrahydro-2(1H)-pyrimidinone, at an elevated temperature, for example in the range 50°–160° C. Alternatively, an ethyl or methyl protecting group may be removed, for example, by reaction with lithium diphenylphosphide in a suitable solvent or diluent, such as tetrahydrofuran or t-butyl methyl ether, at a temperature in the range, for example, 0°–60° C. Similarly, an alkanoyl or benzoyl protecting group may be removed, for example, by base catalysed hydrolysis [such as sodium or potassium hydroxide in an aqueous (1–4C)alkanol or glycol] at a temperature, for example, in the range 10°–60° C. Similarly, an allyl or tetrahydropyran-2-yl protecting group may be removed, for example, by a conventional treatment with a strong acid such as trifluoroacetic acid. Similarly, a trimethylsilyl protecting group may be removed, for example, by conventional treatment with aqueous tetrabutylammonium fluoride or sodium fluoride, and a benzyl or 1-phenylethyl protecting group, for example, by treatment with sodium in liquid ammonia.

The necessary starting materials if formula II may be made using analogous procedures to those described in European patent application, publication No. 94239 (and as illustrated for Rd=methyl in the accompanying Examples). Particularly useful protecting groups Rd include, for example, methyl, allyl, benzyl and tetrahydropyran-2-yl. The reaction sequences involved in the production of these formula II compounds which are valuable chemical intermediates are shown in Scheme 1 starting from the appropriate methyl or ethyl 3-(o-substituted phenyl)-3-oxopropionate. Alternatively, the trifluoromethyl substituent may be introduced at a later stage in the reaction sequence as illustrated in Scheme 2, starting from the appropriate 5(Z)-erythro-9-hydroxy-8-hydroxymethyl-9-(o-substituted phenyl)-5-nonenoic acid, itself conveniently obtained, for example, by acid hydrolysis of the corresponding 5(Z)-7-(2,2-dimethyl-4-[o-substituted phenyl]-1,3-dioxan-5-yl)heptenoic acid (as described hereinafter in Example 1 for Rd=methyl).

(b) Reacting ([2,4,5-cis]-4-o-hydroxyphenyl-2-trifluoromethyl-1,3-dioxan-5-yl)acetaldehyde of the formula III with a Wittig reagent of the formula $(Rf)_3P=CH.(CH_2)_3.CO_2^-M^+$ wherein Rf is (1-6C)alkyl or aryl (especially phenyl) and $M^+$ is a cation, for example an alkali metal cation, such as the lithium, sodium or potassium cation.

The process is conveniently performed in a suitable solvent or diluent, for example an aromatic solvent such as benzene, toluene or chlorobenzene, an ether such as 1,2-dimethoxyethane, t-butyl methyl ether or tetrahydrofuran, in dimethyl sulphoxide or tetramethylene sulphone, or in a mixture of one or more such solvents or diluents. The process is generally performed at a temperature in the range, for example, $-80°$ C. to $40°$ C. but is conveniently performed at or near ambient temperature, that is in the range $0°$ to $35°$ C.

The starting acetaldehyde of formula III may be obtained by analogy with the procedures described for analogous compounds in European patent application, publication No. 94239, for example using the sequence of reactions shown in Scheme 1 herein (e.g. wherein $Rd=Re=$tetrahydropyran-2-yl) to produce the corresponding protected aldehyde of the formula V from which the free acetaldehyde is itself liberated, for example by a conventional treatment with a strong acid such as trifluoroacetic acid. Alternatively, the aldehyde of formula III may be obtained by ozonolysis of the corresponding allyl dioxane of formula VI, itself obtained by deprotection of the corresponding protected derivative of formula VII (as illustrated hereinafter in Example 3 for Rd=methyl) using an analogous deprotection procedure to that described in process (a) hereinbefore.

The necessary Wittig reagents may themselves be obtained by conventional procedures, for example by treating the corresponding phosphonium halides of the formula $(Rf)_3P.^+CH_2.(CH_2)_3CO_2HX^-$, wherein X is a halide anion (for example a bromide or iodide), with a strong base, such as sodium hydride, potassium t-butoxide, lithium diisopropylamide or butyllithium, conveniently in the same solvent or diluent as is used for the Wittig reaction (b). In general, the Wittig reagents are prepared in situ just before carrying out reaction (b).

(c) Hydrolysing a derivative of the formula IV wherein Z is alkoxycarbonyl; phenoxycarbonyl or benzyloxycarbonyl optionally substituted by one or more halogeno, alkyl, alkoxy, nitro or cyano groups; cyano; or carbamoyl.

A suitable value for Z when it is alkoxycarbonyl is, for example, methoxycarbonyl, ethoxycarbonyl or t-butyloxycarbonyl; and when it is optionally substituted phenoxycarbonyl or benzyloxycarbonyl is, for example, p-chlorophenoxycarbonyl, p-methylphenoxycarbonyl, p-methoxyphenoxycarbonyl, phenoxycarbonyl, benzyloxycarbonyl, 4-nitrobenzyloxycarbonyl and 2-cyanobenzyloxycarbonyl.

The hydrolysis may be performed using acid or base catalysis, for example using a strong acid such as hydrochloric, sulphuric or trifluoroacetic acid, or an alkali metal hydroxide such as sodium or potassium hydroxide, in either case, usually in the presence of a suitable aqueous solvent, for example an aqueous (1-4C)alkanol or glycol such as aqueous methanol, ethanol or ethylene glycol. When acid catalysis is used acetic acid may also be used as a solvent. The reaction is generally carried out at a temperature in the range, for example, $15°–120°$ C. In general, higher reaction temperatures are required when Z is cyano or carbamoyl.

The starting derivatives of formula IV may be obtained, for example, by analogy with process (b) hereinabove by reaction of the aldehyde of formula III with a suitable Wittig reagent of the formula $(Rf)_3P=CH.(CH_2)_3.Z$. Alternatively, they may be made, for example, by reacting a protected aldehyde of the formula V with a suitable Wittig reagent of the formula $(Rf)_3P=CH.(CH_2)_3.Z$, followed by removal of the protecting group Rd from the phenolic oxygen in the intermediate obtained.

When a salt of the compound of formula I is required, it is generally obtained by reaction with the appropriate base, or another salt thereof, using a conventional procedure.

Further, when the laevorotatory optically active form of the compound of formula I is required, one of the aforesaid processes (a)–(c) may be carried out using the appropriate optically active starting material. Alternatively, the racemic form of the compound of formula I may be reacted with the appropriate optically active form of a suitable organic base, for example ephedrine or 1-phenylethylamine, followed by conventional separation of the diastereoisomeric mixture of salts thus obtained, for example by fractional crystallisation from a suitable solvent, such as a mixture of ethyl acetate and diethyl ether, whereafter the required laevorotatory optically active form of the compound of formula I may be liberated by a conventional treatment with acid, for example using an aqueous mineral acid such as dilute hydrochloric acid. An example of an appropriate optically active base is (+)-1-phenylethylamine.

The compounds of formula II–VII are novel intermediates encompassed by the invention in racemic form or in the optically active form corresponding to the laevorotatory optically active form of the compound of formula I.

As stated earlier, the compound of formula I shows $TXA_2$ antagonism and in particular antagonises the effects of $TXA_2$ on blood platelets, the vasculature and/or the lung. The $TXA_2$ antagonism may be demonstrated experimentally in one or other of the following standard tests:

(a) The rabbit aortic strip model devised by Piper and Vane (Nature, 1969, 223, 29–35) using as agonist the $TXA_2$ mimetic agent known as U'46619 (e.g. R. L. Jones, et alia, in "Chemistry, Biochemistry and Pharmacological Activity of Prostanoids" eds. S. M. Roberts and F. Scheinmann, at p.211; Pergamon Press, 1979);

(b) a blood platelet aggregation test based on that described by Born (Nature, 1962, 194, 927-929) and involving measuring the inhibition by a test compound of aggregation of citrated, platelet rich, human plasma induced by a sub-maximal concentration (in the range 50–250 ng/ml.) of U46619; and (c) a bronchoconstriction test involving measuring the inhibition by a test compound of the bronchoconstriction induced in the Konzett-Rossler guinea-pig model (as modified by Collier and James, Brit. J. Pharmacol., 1967, 30, 283-307) by intravenous administration of the $TXA_2$ mimetic agent, U46619 at 1–1.9 μg/kg.

Similarly, the antagonism of the effects of $TXA_2$ on the vasculature may be demonstrated in the following manner:

(d) Male rats (Alderley Park strain) are anaesthetised with sodium pentobarbital and blood pressure is monitored at the carotid artery. The $TXA_2$ mimetic agent known as U46619 is administered intravenously via the jugular vein and an $ED_{50}$ (dose necessary to produce 50% of the maximum hypertensive effect) is established (n=3). The $ED_{50}$ for U46619 is approximately 5 μg/kg. The test compound is then administered either intravenously via the jugular vein or orally via a cannula directly into the stomach and the animal challenged with an $ED_{50}$ dose of U46619, five minutes after dosing with test compound and then successively every ten minutes until the hypertensive effect of U46619 is no longer blocked.

Further, the antagonism of the effects of $TXA_2$ on blood platelets may be demonstrated ex vivo using standard tests in laboratory animals such as the rabbit, rat, guinea pig or dog:

(e) For example in the rabbit, arterial blood samples are taken by standard techniques into 3.8% w/v solution of trisodium citrate as anti-coagulant (1 part citrate: 9 parts blood) and then centrifuged first at 150 g, and then at 1000 g, to prepare platelet rich and platelet poor plasma fractions. These fractions are then used to calibrate an instrument for measuring light transmittance and thus the amount of platelet aggregation. The extent of platelet aggregation following addition of the $TXA_2$ mimetic agent U46619 (final concentrations 0.2–2.2 μg./ml.) to the platelet rich plasma fraction is then determined, and the value of maximum aggregation in response to each concentration of U46619 is recorded. The test animals are then dosed orally with the test compound, and arterial blood samples are withdrawn at intervals after dosing. The platelet rich plasma fraction is prepared and U46619 added as above, and the extent of aggregation assessed by measuring the light transmittance of the sample. This value is compared with that obtained from the same animal before dosing, so that a measure of the extent of inhibition of U46619 induced blood platelet aggregation is obtained.

A similar procedure is used in rats and guinea pigs except that blood samples are not taken prior to dosing but a control value is obtained from a group of undosed animals. When the aggregation of dog platelets is being studied, it is necessary to use a predetermined, threshold concentration of the platelet aggregant adenosine diphosphate (about $0.4–1.2 \times 10^{-6}M$) together with the $TXA_2$ mimetic agent, U46619.

Using the above test procedures, the following representative results have been obtained with the compound of formula I in racemic form:

(a) $pA_2$ 7.73±0.05;

(b) $IC_{50}$ 7.78±1.6 ng./ml;

(c) ca 95% reduction of bronchoconstriction at 0.5 mg./kg. p.o. 2.5 hours after administration;

(d) essentially complete protection from blood pressure rise induced by the $TXA_2$ mimetic agent U46619, 3 hours after oral administration at 5 mg./kg.;

(e) 95% inhibition of U46619 induced aggregation 12 hours after oral administration to dogs at 2.5 mg./kg.; and 90% inhibition of U46619 induced aggregation 6.5 hours after oral administration to rats at 10 mg./kg.

The above results indicate the unexpectedly superior $TXA_2$ antagonism shown by the compound of formula I compared with that of the racemic form of the closest structurally analogous compounds in European patent application, publication number 94239 i.e. 5(Z)-7-(4-o-hydroxyphenyl-2,2-dimethyl-1,3-dioxan-cis-5-yl)heptenoic acid (P) and 5(Z)-7-([2,4,5-cis]-4-phenyl-2-trifluoromethyl-1,3-dioxan-5-yl)heptenoic acid (Q). Thus, for example, although the latter compounds possess similar $pA_2$ values in vitro in procedure (a) (P, $pA_2$ 7.5±0.05; Q, 6.52±0.02), in vivo the compounds P and Q are unexpectedly both less potent and have a shorter duration of biological action.

For example, in procedure (e), the racemic form of the formula I compound produces essentially complete inhibition of U46619 induced platelet aggregation for up to 12 hours following an oral dose of 2.5 mg./kg. in dogs. By contrast, the racemic form of P produces a maximal 93% inhibition of platelet aggregation some 3 hours after an oral dose of 2.5 mg./kg.in dogs with this inhibition falling to 15% after 12 hours. Similarly, the racemic form of Q only produces a maximal 23% inhibition of platelet aggregation some 4 hours after an oral dose of 75 mg./kg. in dogs.

Additionally, in the procedure (c), the racemic form of P produced only 57% inhibition of bronchoconstriction 2.5 hours after oral dosing at 0.5 mg./kg., and at the same dose the racemic form of Q produced no significant inhibition after 2.5 hours, whereas, as stated above, the racemic form of the formula I compound produced ca 95% inhibition 3 hours after oral dosing at 0.5 mg./kg.

The compound of formula I may be used in the therapy or prevention of diseases or adverse conditions in warm-blooded animals in which it is desirable to antagonise one or more of the actions of $TXA_2$. In general, the compound of formula I will be administered for this purpose by an oral, rectal, intravenous, subcutaneous, intramuscular or inhalation route, so that a dose in the range, for example 0.05–10 mg./kg. body weight, will be given up to four times per day, varying with the route of administration, the severity of the condition and the size and age of the patient under treatment, according to practices known in the medical art.

The compound of formula I will generally be used in the form of a pharmaceutical composition comprising the compound of formula I in racemic or laevorotatory optically active form, or a physiologically acceptable salt thereof, together with a pharmaceutically acceptable diluent or carrier. Such compositions are provided as a further feature of the invention and may be in a variety of dosage forms. For example, they may be in the form of tablets, capsules, solutions or suspensions for oral administration; in the form of suppositories for rectal administration; in the form of sterile solutions or suspensions for administration by intravenous or intramuscular injection; in the form of aerosols or nebuliser solutions or suspensions for administration by inhalation; and in the form of powders together with pharmaceutically acceptable inert solid diluents such as lactose for administration by insufflation.

The pharmaceutical compositions may be obtained by conventional procedures using pharmaceutically acceptable diluents and carriers well known in the art. Representative compositions are given in the accompanying Examples.

Tablets and capsules for oral administration may conveniently be formed with an enteric coating, for example comprising cellulose acetate phthalate.

The pharmaceutical compositions of the invention may also contain one or more agents known to be of value in diseases or conditions intended to be treated; for example, a known platelet aggregation inhibitor, hypolipidemic agent, anti-hypertensive agent, beta-adrenergic blocker or a vasodilator may usefully also be present in a pharmaceutical composition of the invention for use in treating a heart or vascular disease or condition. Similarly, by way of example, an anti-histamine, steroid (such as beclomethasone dipropionate), sodium cromoglycate, phosphodiesterase inhibitor or a beta-adrenergic stimulant may usefully also be present in a pharmaceutical composition of the invention for use in treating a pulmonary disease or condition.

In addition to its use in medicine the compound of formula I is also useful as a pharmacological tool in the development and standardisation of test systems for the evaluation of the effects of $TXA_2$ in laboratory animals such as cats, dogs, rabbits, monkeys, rats and mice, as part of the search for new therapeutic agents. The compound of formula I may also be used because of its $TXA_2$ antagonist properties in helping to maintain the viability of blood and blood vessels in warm-blooded animals (or parts thereof) under-going artificial extra-corporeal circulation, for example during limb or organ transplants. When used for this purpose, the compound of formula I, in racemic or laevorotatory optically active form, or a physiologically acceptable salt thereof, will generally be administered so that a steady state concentration in the range, for example 0.5 to 50 mg. per liter is achieved in the blood.

The invention will now be illustrated in the following non-limiting Examples in which, unless otherwise stated:

(i) evaporations and concentrations were carried out by rotary evaporation in vacuo using a bath temperature of up to 45° C.;

(ii) operations were carried out at ambient temperature, that is in the range 18°–26° C.

(iii) column chromatography was performed on Merck Kieselgel 60 (Art 7734), using about 50–70 g. of $SiO_2$ per g. of sample and monitoring the process by thin layer chromatography (TLC) on Merck 0.25 mm. Kieselgel 60F 254 plates (Art 5715); flash chromatography and medium pressure liquid chromatography (MPLC) were performed on Merck Kieselgel 60(Art 9385) monitoring the process by TLC on Merck 0.25 mm Kieselgel 60F 254 plates (Art. 5715) and UV absorption at 254 nm, respectively; the chromatography materials were obtained from E. Merck, Darmstadt, W. Germany;

(iv) yields are given for illustration only and are not necessarily the maximum attainable;

(v) NMR spectra were determined at 90 MHz or 400 MHz (when indicated by an asterisk) in $CDCl_3$ using tetramethylsilane (TMS) as an internal standard, and are expressed as chemical shifts (delta values) in parts per million relative to TMS, with the following typical abbreviations for the designation of major peaks: s, singlet; m, multiplet; t, triplet; br, broad, d, doublet; q, quartet; when a single chemical shift value is given for a multiplet (m) this corresponds to the centre point of the signals making up the multiplet;

(vi) end-products were isolated as racemates, and characterized by NMR and mass spectrosopy and other standard procedures; and (vii) melting points were determined using a Koffler block apparatus or (**) by differential scanning calorimetry in a sealed capsule.

EXAMPLE 1

5(Z)-7-([2,4,5-cis]-4-o-Methoxyphenyl-2-trifluoromethyl-1,3-dioxan-5-yl)heptenoic acid (19.4 g.) was added to a stirred solution of sodium thioethoxide (25.2 g.) in dry 1,3-dimethyl-3,4,5,6-tetrahydro-2(1H)-pyrimidinone (DMPU) (300 ml.) at 80°–85° C. under argon. The mixture was stirred for 2.25 hours, cooled to 10° C. and poured into an ice-water mixture (1 l.) The aqueous mixture was extracted with dichloromethane (2×500 ml.), acidified to pH3 with 2M hydrochloric acid and extracted with ether (3×500 ml.). The combined extracts were washed with water (3×300 ml.), then with saturated brine (2×300 ml.), then dried ($MgSO_4$) and the solvent evaporated. The oil obtained was purified by flash chromatography eluting with toluene/ethyl acetate/acetic acid (80:20:2 v/v). Recrystallisation from 15% v/v ether/hexane(150 ml.) gave 5(Z)-7-([2,4,5-cis]-4-o-hydroxyphenyl-2-trifluoromethyl-1,3-dioxan-5-yl)heptenoic acid (11.6 g.), m.p. 93°–95° C.; (m.p.** 96.6° C.; peak temperature; heating rate 10° C./minute);

NMR*:1.63 (2H, m), 1.84 (2H, m), 1.97 (2H, q J=7 Hz), 2.28 (2H, t J=7 Hz), 2.55 (1H, m), 4.02 (1H, dm J=12 Hz), 4.25 (1H, d J=12 Hz), 5.11 (1H, q J=3 Hz), 5,28 (1H, m), 5.31 (1H, d J=2 Hz), 5.43 (1H, m), 6.81 (1H, d J=7 Hz), 6.93 (1H, t J=7 Hz), 7.17 (2H, m); m/e 374 (M+);

calculated for $C_{18}H_{21}F_3O_5$: C, 57.7; H, 5.65%; found: C, 57.7; H, 5.7%.

The necessary starting material was obtained as follows:

(a) Starting from (4,5-cis)-5-allyl-4-o-methoxyphenyl-2,2-dimethyl-1,3-dioxane:

(i) A solution containing (4,5-cis)-5-allyl-4-o-methoxyphenyl-2,2-dimethyl-1,3-dioxane (51.60 g.), water (120 ml.) and 2M hydrochloric acid (5.0 ml.) in tetrahydrofuran (THF) (400 ml.) was heated with stirring at 70° C. for 2 hours. The mixture was poured into water (1 l.), then extracted with ether (3×500 ml.). The combined extracts were washed with water (2×250 ml.), then with brine (2×250 ml.), dried ($MgSO_4$) and evaporated to give erythro-2-allyl-1-o-methoxyphenyl-1,3-propanediol (A) as a crystalline solid (43.69 g.), m.p. 59°–60° C.;

NMR: 2.05 (3H, m), 2.65 (2H, s), 3.70 (2H, m) 3.84 (3H, s), 5.06 (3H, m), 5,78 (1H, m), 6.93 (2H, m), 7.25 (1H, td J=7, 2 Hz), 7.42(1H, dd J=7, 2 Hz); m/e 222 (M+);

calculated for $C_{13}H_{18}O_3$: C, 70.3; H, 8.1%; found C, 70.2; H, 8.1%.

(ii) A solution of p-toluenesulphonyl chloride (43.4 g.) in dichloromethane (120 ml.) was added during 30 minutes to a stirred solution of A (44.69 g.) in dichloromethane (400 ml.) containing triethylamine (31.50 ml.) and maintained at 4° C. The mixture was stirred for a further 1 hour at 4° C. and then for 64 hours at ambient temperature before being diluted with ether (1.2 l.). The subsequent mixture was washed successively with water (2×200 ml.), 0.2M aqueous hydrochloric acid (200 ml.), saturated brine (200 ml.), 2% w/v aqueous sodium hydrogen carbonate (200 ml.), water (2×200 ml.) and then with saturated brine (200 ml.). The organic phase was dried ($MgSO_4$) and evaporated. The oil obtained was triturated with 5% v/v ethyl acetate/hexane to give a solid which was recrystallised from 1:3 v/v ethyl acetate/hexane (500 ml.). There was thus obtained 3-(erythro-2-allyl-1-o-methoxyphenyl-1,3-propanediol) p-toluenesulphonate ester (B)(54.4 g.), m.p. 103°–104° C.;

NMR: 2.20 (3H, m), 2.46 (3H, s), 3.83 (3H, s), 4.00 (2H, m), 4.88 (2H, m), 4.97 (1H, d J=1.5 Hz), 5.56 (1H, m), 6.88 (2H, m), 7.22 (2H, m), 7.30 (2H, d J=8 Hz), 7.75 (2H, d J=8 Hz); m/e 394 (M+$NH_4$)+;

calculated for $C_{20}H_{29}O_5S$: C, 63.8; H, 6.4; S, 8.5%; found: C, 64.1; H, 6.6; S, 8.4%.

(iii) A solution of B (54.4 g.) in dry THF (600 ml.) was treated with anhydrous trifluoroacetaldehyde (prepared from 50 g. of trifluoroacetaldehyde methyl hemiacetal) at −78° C. under argon. The mixture was stirred for 1 hour at −78° C. allowed to warm to ambient temperature and stirred for a further 1 hour. Anhydrous potassium carbonate (38.72 g.) was added and the stirred mixture was heated at 70° C. for 16 hours. The mixture was separated by filtration and the residue was washed with further THF. Evaporation of the filtrate and flash chromatography of the residue, eluting with 2% v/v ethyl acetate/hexane, gave [2,4,5-cis]-5-allyl-4-o-methoxyphenyl-2-trifluoromethyl-1,3-dioxane(C) (35.0 g.) as a crystalline solid, m.p. 43°–45° C.;

NMR: 1.90 (2H, m), 2.35 (1H, m), 3.84 (3H, s), 4.01 (1H, bd J=11 Hz), 4.28 (1H, bd J=11 Hz), 5.00 (3H, m), 5.32 (1H, d J=2 Hz), 5.56 (1H, m), 6.86 (1H, dd J=7, 2 Hz), 6.98 (1H, td J=7, 2 Hz), 7.28 (1H, td J=7, 2 Hz), 7.43 (1H, dd J=7, 2 Hz) m/e 302 (M+);

calculated for $C_{15}H_{17}O_3F_3$: C, 59.6, H, 5.6%; found: C, 60.0; H, 5.8%.

(iv) Ozone was passed through a solution of C (35.0 g.) in ethyl acetate (800 ml.) at −78° C. until a permanent blue colour developed. The solution was then flushed with argon until colourless. A solution of triphenylphosphine (45.55 g.) in ethyl acetate (200 ml.) was added and the mixture was allowed to warm to ambient temperature overnight. After evaporation, ether (500 ml.) was added to the residue and the insoluble triphenylphosphine oxide was removed by filtration. The filtrate was evaporated. The oil obtained was purified by flash chromatography, eluting with first 10% and then 25% v/v ethyl acetate/hexane, to give ([2,4,5-cis]-4-o-methoxyphenyl-2-trifluoromethyl-1,3-dioxan-5-yl)acetaldehyde (D) (33.25 g.), m.p. 67°–68° C.;

NMR: 2.60 (3H, m), 3.80(3H, s), 4.17 (2H, bs), 5.08(1H, q J=3 Hz), 5.27 (1H, d J=1.5 Hz), 6.82 (1H, dd J=7, 2 Hz), 6.96 (1H, td J=7, 2 Hz), 7.23 (1H, m), 7.37 (1H, dd J=7, 2 Hz), 9.52 (1H, s); m/e 304 (M+);

calculated for $C_{14}H_{15}O_4F_3$: C, 55.3; H, 4.9%; found: C, 55.4; H, 5.1%.

(v) A solution of D (33.25 g.) in dry THF (150 ml.) was added under argon with stirring and ice-cooling to a solution of the ylid prepared from (4-carboxybutyl)triphenylphosphonium bromide (121.05 g.) and potassium t-butoxide (61.21 g.) in dry THF (750 ml.). The mixture was stirred for 1 hour at 4° C. then overnight at ambient temperature and was then poured into ice-water (1.5 l.). The mixture obtained was extracted with 50% v/v ether/hexane (2×500 ml.) to remove the bulk of neutral material. The aqueous phase was then acidified to pH 2–3 with 2M hydrochloric acid and extracted with ether (4×400 ml.). These combined extracts were washed with water (3×250 ml.), then with saturated brine (2×200 ml.), dried (MgSO4) and evaporated to give a give a yellow oil. Purification by flash chromatography, eluting with toluene/ethyl acetate/acetic acid (85:15:2 v/v) gave a solid (40.15 g.). Recrystallisation from hexane (600 ml.) gave 5(Z)-7-([2,4,5-cis]-4-o-methoxyphenyl-2-trifluoromethyl-1,3-dioxan-5-yl)heptenoic acid (36.2 g.), m.p. 104°–105.5° C.; NMR*: 1.62 (3H, m), 1.92 (1H, m), 2.00 (2H, q J=7 Hz), 2.28 (2H, t J=7 Hz), 2.49 (1H, m), 3.83 (3H, s), 4.01 (1H, dm J=12 Hz), 4.20 (1H, d J=12 Hz), 5.11 (1H, q J=3 Hz), 5.21 (1H, m), 5.32 (1H, d J=2 Hz), 5.39 (1H, m), 6.87 (1H, d J=7 Hz), 7.00 (1H, t J=7 Hz), 7.28 (1H, m), 7.43 (1H, m); m/e 388 (M+);

calculated for $C_{19}H_{23}F_3O_5$: C, 58.8; H, 5.9%; found: C, 58.7; H, 6.0%

(b) Starting from 5(Z)-erythro-9-hydroxy-8-hydroxymethyl-9-o-methoxyphenyl-5-nonenoic acid:

(i) A solution containing 5(Z)-erythro-9-hydroxy-8-hydroxymethyl-9-o-methoxyphenyl-5-nonenoic acid (7.70 g.) and ethyl acetate (10 ml.) in ether (25 ml.) was treated at 4° C. with an ice-cold ethereal solution of diazomethane until a yellow colour persisted. The solution was then treated with acetic acid (0.2 ml.) and the solvent removed in vacuo. The residual oil was purified by flash chromatography, eluting with 45% v/v ethyl acetate/hexane, to give methyl 5(Z)-erythro-9-hydroxy-8-hydroxymethyl-9-o-methoxyphenyl-5-nonenoate (E) as a colourless oil (7.83 g.);

NMR*: 1.74 (2H, m), 1.89 (1H, m), 2.05 (3H, m), 2.30(3H, m), 2.47 (1H, bs), 3.13 (1H, d J=4 Hz), 3.66 (3H, s), 3.68 (2H, m), 3.84 (3H, s), 5.21 (1H, t J=4 Hz), 5.37 (1H, m), 6.88 (1H, d J=7 Hz), 6.99 (1H, t J=7 Hz), 7.2 (1H, m), 7.43 (1H, dd J=7, 2 Hz); m/e 340 (M+NH4)+;

calculated for $C_{18}H_{26}O_5$: C, 67.1; H, 8.1%; found: C, 67.3; H, 8.1%.

(ii) A solution of p-toluenesulphonyl chloride (5.27 g.) in dichloromethane (25 ml.) was added over 30 minutes to a stirred solution of E (7.68 g.) in dichloromethane (50 ml.) containing triethylamine (3.84 ml.) maintained at 4° C. The mixture was then stirred for a further 1 hour at 4° C. and then for 64 hours at ambient temperature before being diluted with ether (200 ml.). The subsequent mixture was washed successively with water (2×40 ml.), 0.1M hydrochloric acid (40 ml.), saturated brine (40 ml.), 2% w/v sodium hydrogen carbonate solution (40 ml.), water (2×40 ml.) and then saturated brine (40 ml.). The organic phase was dried (MgSO4) and evaporated. The residual oil was purified by flash chromatography, eluting with first 25%, and then 35% and finally 50% v/v ethyl acetate/hexane to give methyl 5(Z)-erythro-9-hydroxy-9-o-methoxyphenyl-8-(p-toluenesulphonyloxymethyl)-5-nonenoate (F) as a colourless oil (8.56 g.);

NMR: 1.97 (9H, m), 2.40 (3H, s), 3.60 (3H, s), 3.75 (3H, s), 3.95 (2H, m), 4.88 (1H, m), 5.23 (2H, m), 6.80 (2H, m), 7.18 (2H, m), 7.24 (2H, d J=8 Hz), 7.65 (2H, d J=8 Hz;); m/e 494 (M+NH4)+;

calculated for $C_{25}H_{32}O_7S$: C, 63.0; H, 6.7; S, 6.7%; found: C, 62.6; H, 6.5; S, 6.6%.

(iii) A solution of F (2.38 g.) in dry THF (20 ml.) was treated under argon with anhydrous trifluoroacetaldehyde (prepared from 2.16 g. of trifluoroacetaldehyde ethyl hemiacetal) at −78° C. The mixture was stirred for 1 hour at −78° C. and then allowed to warm to ambient temperature and stirred for a further 1 hour. Anhydrous potassium carbonate (1.38 g.) was next added. The mixture was stirred at 60° C. for 16 hours, diluted with ether (60 ml.) and then washed with water (3×15 ml.), followed by saturated brine (2×15 ml.). The organic phase was dried (MgSO4) and the solvent evaporated to give crude methyl 5(Z)-([2,4,5-cis]-4-o-methoxyphenyl-2-trifluoromethyl-1,3-dioxan-5-yl)-heptenoate as an oil.(F*). The crude oil was dissolved in methanol (120 ml.). 2M Potassium hydroxide (15.0 ml.) was then added and the mixture was stirred overnight. 2M Hydrochloric acid (10 ml.) was next added and the mixture was concentrated in vacuo, diluted with water (75 ml.) and washed with 50% v/v ether/hexane (2×50 ml.). The aqueous phase was acidified to pH3 with 2M hydrochloric acid and extracted with ether (3×50 ml.). The latter combined extracts were washed with water (3×30 ml.), then with saturated brine (30 ml.), dried (MgSO$_4$) and evaporated to give an oil which crystallised on standing. Recrystallisation from hexane (45 ml.) gave 5(Z)-7-([2,4,5-cis]-4-o-methoxyphenyl-2-trifluoromethyl-1,3-dioxan-5-yl)heptenoic acid (1.29 g.), m.p. 101°–102° C., essentially identical to the sample prepared in [a](v) above.

[Note: A portion of the crude ester F* was purified by MPLC, using 10% v/v ethyl acetate/hexane as eluant, to give the pure ester methyl 5(Z)-7-([2,4,5-cis]-4-o-methoxyphenyl-2-trifluoromethyl-1,3-dioxan-5-yl)heptenoate as an oil;

NMR*: 1.60 (3H, m), 1.96 (3H, m), 2.23 (2H, t J=7 Hz), 2.49 (1H, m), 3.66 (3H, s), 3.81 (3H, s), 4.01 (1H, dm J=12 Hz), 4.18 (1H, br d J=12 Hz), 5.10 (1H, q J=3 Hz), 5.18 (1H, m), 5.30 (1H, d J=2 Hz), 5.37 (1H, m), 6.86 (1H, br d J=7 Hz), 7.00 (1H, br t J=7 Hz), 7.28 (1H, td J=8, 1.5 Hz), 7.43 (1H, dd J=7, 1.5 Hz); m/e 402 (M+).]

The starting 5(Z)-erythro-9-hydroxy-8-hydroxymethyl-9-o-methoxyphenylnonenoic acid was obtained as follows:

A solution containing 5(Z)-7-(2,2-dimethyl-4-o-methoxyphenyl-1,3-dioxan-cis-5-yl)heptenoic acid (10.0 g.), water (33 ml.) and 2M hydrochloric acid (0.5 ml.) in THF (267 ml.) was heated with stirring at 60°–70° C. for 2 hours. The solvent was then evaporated. The residue obtained was diluted with ether (350 ml.). The mixture was washed with water (4×75 ml.), then with saturated brine (2×75 ml.), dried (MgSO$_4$) and evaporated. The oil obtained was purified by flash chromatography, eluting with toluene/ethyl acetate/acetic acid (60:40:2 v/v), to give 5(Z)-erythro-9-hydroxy-8-hydroxymethyl-9-o-methoxyphenylnonenoic acid as a colourless oil which slowly crystallised to give solid (8.40 g.), m.p. 79°–80° C.;

NMR*: 1.66 (2H, m), 1.90 (1H, m), 2.08 (3H, m), 2.32(3H, m), 3.69 (2H, m), 3.82 (3H, s), 5.22 (1H, d J=4 Hz), 5.37 (2H, m), 6.88 (1H, d J=8 Hz), 6.98 (1H, t J=7 Hz), 7.25(1H, m), 7.43 (1H, dd J=7, 2 Hz) ppm; m/e 326 (M+NH$_4$)+;

calculated for C$_{17}$H$_{24}$O$_5$: C, 66.2; H, 7.8%; found: C, 66.5; H, 7.7%.

EXAMPLE 2

A solution of 5(Z)-7-([2,4,5-cis]-4-o-hydroxyphenyl-2-trifluoromethyl-1,3-dioxan-5-yl)heptenoic acid (5.88 g.) in 10% v/v ethyl acetate in ether (60 ml.) was treated with (+)-1-phenylethylamine (1.0 ml.). The crystalline salt (2.91 g.) which separated was collected by filtration and recrystallised from ethyl acetate/ether to constant optical rotation. After three recrystallisations optically pure salt (X) was obtained as needles (1.59 g.) $^{20}[\alpha]_D$−78.2° (c, 1.0, MeOH), m.p.** 150.2° C. (peak temperature, heating rate 5° C./minute).

The salt X (1.59 g.) was suspended in ether (30 ml.) and washed successively with 0.5M hydrochloric acid (3×20 ml.), water (3×20 ml.) and brine (20 ml.). The ether solution was dried (MgSO$_4$) and evaporated to give an oil which slowly crystallised to give solid (1.08 g.), $^{20}[\alpha]_D$−126.3° (c, 1.0, MeOH). This solid (which contained above 5% w/w of the corresponding 5(E) isomer by analytical techniques) was purified by medium pressure chromatography on silica using a mixture of hexane, ether and acetic acid (75:25:1 v/v) as eluant to give (−)-5(Z)-7-([2,4,5-cis]-4-o-hydroxyphenyl-2-trifluoromethyl-1,3-dioxan-5-yl)heptenoic acid; $^{20}[\alpha]_D$−133.5° (c, 1.0, MeOH);

m.p.** 113.8° C. (peak temperature, heating rate 5° C./minute.) [$^{23}[\alpha]_D$−143.4° (c, 1.0, MeOH);

m.p.** 114.8° C. (peak temperature, heating rate 5° C./minute) after recrystallisation from 10% v/v ether/hexane];

NMR: 1.62 (2H, m), 1.84 (2H, m) 1.98 (2H, q J=7 Hz), 2.29 (2H, t J=7 Hz), 2.56 (1H, m), 4.01 (1H, dm J=12 Hz), 4.24 (1H, d J=12 Hz), 5.11 (1H, q J=3 Hz), 5.29 (1H, m), 5.32 (1H, d J=2 Hz), 5.42 (1H, m), 6.82 (1H, d J=7 Hz); 6.93 (1H, t J=7 Hz), 7.18 (2H, m) ppm; m/e 374 (M+); calculated for C$_{18}$H$_{21}$F$_3$O$_5$: C, 57.7; H, 5.65%; found: C, 57.8; H, 5.9%.

EXAMPLE 3

A solution of ([2,4,5-cis]-4-o-hydroxyphenyl-2-trifluoromethyl-1,3-dioxan-5-yl)acetaldehyde (363 mg.) in dry THF (3 ml.) was added under argon with stirring to an ice-cooled solution of the ylid prepared from (4-carboxybutyl)triphenylphosphonium bromide (1.66 g.) and potassium t-butoxide (840 mg) in dry THF (15 ml.). The mixture was stirred for 30 minutes at 40° C., for 30 minutes at ambient temperature and was then poured into ice-water (50 ml.). The aqueous mixture was washed with ether (2×20 ml.) to remove the bulk of neutral material. The aqueous phase was acidified to pH 3 with 2M hydrochloric acid and extracted with ether (3×25 ml.). These combined extracts were washed successively with water (3×15 ml.) and saturated brine (15 ml.), dried (MgSO$_4$) and evaporated. The yellow, oily residue was purified by MPLC, eluting with hexane/ethyl acetate/acetic acid (70:30:1 v/v). The crystalline solid (401 mg.) obtained was recrystallized from 12.5% v/v ether/hexane (8 ml.) to give 5(Z)-7-([2,4,5-cis]-4-o-hydroxyphenyl-2-trifluoromethyl-1,3-dioxan-5-yl)heptenoic acid (290 mg.), m.p. 94°–96° C.;

calculated for C$_{18}$H$_{21}$F$_3$O$_5$: C, 57.7; H, 5.65%; found C, 57.6; H, 5.7%; having an essentially identical NMR and mass spectrum to that described in Example 1.

The necessary starting aldehyde was obtained as follows:

(i) A solution of [2,4,5-cis]-5-allyl-4-o-methoxyphenyl-2-trifluoromethyl-1,3-dioxane (C) (1.22 g.) in dry THF (4 ml.) was treated at 4° C. under argon with a solution of lithium diphenylphosphide [prepared from chlorodiphenylphosphine (2.23 g.) and lithium metal (283 mg.) in dry THF (12 ml.)]. The mixture was stirred for 15 minutes at 4° C., for 3 hours at 50° C., then cooled to 10° C. and poured into an ice-water mixture (50 ml.). The aqueous mixture was acidified to pH 3 with 2M hydrochloric acid and extracted with ether (3×30 ml.). The combined extracts were washed successively with water (4×15 ml.) and saturated brine (15 ml), then dried (MgSO$_4$) and evaporated. The residual oil was purified by MPLC, eluting with hexane/ethyl acetate/acetic acid (82.5:17.5:0.1 v/v), to give [2,4,5-cis]-5-allyl-4-o-hydroxyphenyl-2-trifluoromethyl-1,3-dioxane (G), as a colourless oil which slowly crystallised to give solid (1.11 g), m.p. 80°–81.5° C.;

NMR (200 MHz): 1.88 (1H, m), 2.00 (1H, m), 2.49 (1H, m), 4.02 (1H, dt J=12, 1.5 Hz), 4.33 (1H, dd J=12, 1 Hz), 5.05 (2H, m), 5.10 (1H, q J=3 Hz), 5.33 (1H, d J=2 Hz), 5.58 (1H, m), 6.41 (1H, s) 6.82 (1H, dd J=7, 1

Hz), 6.92 (1H, td J=7, 1 Hz), 7.11 (1H, dd J=7, 1.5 Hz), 7.20 (1H, td J=7, 1.5 Hz); m/e 306 (M+NH$_4$)+;

calculated for C$_{14}$H$_{15}$F$_3$O$_3$: C, 58.3; H, 5.2%; found C, 58.1; H, 5.2%.

(ii) Ozone was passed through a solution of G (1.0 g) in ethyl acetate (75 ml.) at −78° C. until a permanent blue colour developed. The solution was then flushed with argon until colourless. A solution of triphenylphosphine (1.37 g.) in ethyl acetate (20 ml.) was added and the mixture was stirred for 1 hour at −78° C. and then overnight at ambient temperature. The solvent was evaporated and the residue was purified by flash chromatography, eluting with 30% v/v ethyl acetate/hexane, to give ([2,4,5-cis]-4-o-hydroxyphenyl-2-trifluoromethyl-1,3-dioxan-5-yl)acetaldehyde as a crystalline solid (766 mg.), m.p. 140°–142° C.;

NMR (200 MHz): 2.51 (1H, br dd J=18, 3 Hz), 2.64 (1H, m), 2.98 (1H, dd J=18, 9 Hz), 4.19 (2H, m), 5.11 (1H, q J=3 Hz), 5.32 (1H, d J=2 Hz), 6.17 (1H, s), 6.79 (1H, br d J=8 Hz), 6.93 (1H, td J=7, 1 Hz), 7.19 (2H, m), 9.61 (1H, s); m/e 308 (M+NH$_4$)+;

calculated for C$_{13}$H$_{13}$F$_3$O$_4$: C, 53.8; H, 4.5%; found: C, 53.7; H, 4.6%.

The starting dioxane derivative C was obtained using a variation of the procedure described in part (a) (iii) of Example 1, in which the p-toluenesulphonate ester (B) (2.26 g.) was reacted with trifluoroacetaldehyde ethyl hemiacetal (1.73 g.) (instead of anhydrous trifluoroacetaldehyde) in the presence of anhydrous potassium carbonate (1.66 g.) in dry THF (20 ml.) initially at ambient temperature and then for 16 hours at 60° C.

EXAMPLE 4

Using a similar procedure to that described in Example 1, but starting from (−)-5(Z)-7-([2,4,5-cis]-4-o-methoxyphenyl-2-trifluoromethyl-1,3-dioxan-5-yl)heptenoic acid, there was obtained after flash chromatography, eluting with toluene/ethyl acetate/acetic acid (85:15:2 v/v) and MPLC, eluting with hexane/ethyl acetate/acetic acid (75:25:1 v/v), followed by recrystallisation of the resultant solid from 10% v/v ether/hexane, (−)-5(Z)-7-([2,4,5-cis]-4-o-hydroxyphenyl-2-trifluoromethyl-1,3-dioxan-5-yl)heptenoic acid;

m.p.** 114.7° C. (peak temperature, heating rate 5° C./minute);

$^{23}[\alpha]_D$ −141.8° (c, 1.0, MeOH); having an NMR spectrum essentially identical to that given in Example 2;

m/e 374 (M+);

calculated for C$_{18}$H$_{21}$F$_3$O$_5$: C, 57.7; H, 5.65%; found: C, 57.4; H, 5.6%.

The necessary starting material may be prepared using the procedure described in Example 1(b), parts (i)–(iii), starting from (−)-erythro-5(Z)-9-hydroxy-8-hydroxymethyl-9-o-methoxyphenylnonenoic acid [itself obtained as described in European patent application, publication No. 142,323] and was obtained as a colourless oil (1.71 g.), $^{23}[\alpha]_D$ −127.6° (c, 1.0, MeOH);

NMR (200 MHz): 1.63 (3H, m), 1.99 (3H, m), 2.29 (2H, t J=7 Hz), 2.50 (1H, m), 3.80 (3H, s), 4.00 (1H, dm J=12 Hz), 4.20 (1H, d J=12 Hz), 5.12 (1H, q J=3 Hz), 5.21 (1H, m), 5.32 (1H, d J=2 Hz), 5.37 (1H, m), 6.86 (1H, d J=7 Hz), 7.00 (1H, t J=7 Hz), 7.28 (1H, t d J=7, 1.5 Hz), 7.44 (1H, dd J=7, 1.5 Hz); m/e 388 (M+).

The intermediate (−)-methyl 5(Z)-7-([2,4,5-cis]-4-o-methoxyphenyl-2-trifluoromethyl-1,3-dioxan-5-yl)heptenoate, obtained during step (iii), was isolated as a colourless oil (after MPLC using 12.5% v/v ethyl acetate/hexane as eluant), $^{23}[\alpha]_D$ −133.6° (c, 1.0, MeOH), with an NMR spectrum essentially identical to that of the corresponding racemic ester F*.

EXAMPLE 5

(a) A stirred mixture of methyl 5(Z)-7-([2,4,5-cis]-4-o-hydroxyphenyl-2-trifluoromethyl-1,3-dioxan-5-yl)heptenoate (58.2 mg.), THF (2 ml.) and 2M hydrochloric acid (1 ml.) was heated at 55° C. for 20 hours. Water (10 ml.) was added and the mixture was extracted with ethyl acetate (2×5 ml.). The combined extracts were washed with water (3×2 ml.), then with saturated brine (2 ml.); dried (MgSO$_4$); and evaporated. The residue was purified by MPLC, eluting with hexane/ethyl acetate/acetic acid (75:25:1 v/v), to give 5(Z)-2-([2,4,5-cis]-4-o-hydroxyphenyl-2-trifluoromethyl-1,3-dioxan-5-yl)heptenoic acid, essentially identical to the material isolated in Example 1, as judged by thin layer chromatography (TLC) and high pressure liquid chromatography (HPLC).

(b) A solution of methyl 5(Z)-7-([2,4,5-cis]-4-o-hydroxyphenyl-2-trifluoromethyl-1,3-dioxan-5-yl)heptenoate (58.2 mg.) in THF (4.5 ml.) was treated with 2M potassium hydroxide (0.503 ml.) and the mixture stirred for 20 hours. Water (10 ml.) was added and the mixture was washed with 50% v/v ether/hexane (5 ml.). The aqueous phase was acidified to pH 3 with 2M hydrochloric acid and extracted with ethyl acetate (2×5 ml.). These combined extracts were washed with water (3×2 ml.) then with saturated brine (2 ml.); dried (MgSO$_4$); and evaporated. Purification of the residue by MPLC, eluting with hexane/ethyl acetate/acetic acid (75:25:1 v/v), gave 5(Z)-7-([2,4,5-cis]-4-o-hydroxyphenyl-2-trifluoromethyl-1,3-dioxan-5-yl)heptenoic acid, essentially identical to the material isolated in Example 1, as judged by TLC and HPLC.

The necessary starting material may be obtained, for example, by reaction of the Wittig reagent Ph$_3$P=CH.(CH$_2$)$_3$CO$_2$CH$_3$ with ([2,4,5-cis]-4-o-hydroxyphenyl-2-trifluoromethyl-1,3-dioxan-5-yl)acetaldehyde, using a similar procedure to that described in Example 3. However, a reference sample may also be obtained as follows:

5(Z)-7-([2,4,5-cis]-4-o-Hydroxyphenyl-2-trifluoromethyl-1,3-dioxan-5-yl)heptenoic acid in ether was treated at 4° C. with an ethereal solution of diazomethane until a permanent yellow colour persisted for 2 minutes. Acetic acid (1 drop) was added and the solvent evaporated. Flash chromatography of the residue, eluting with 25% v/v ethyl acetate/hexane, gave methyl 5(Z)-7-([2,4,5-cis]-4-o-hydroxyphenyl-2-trifluoromethyl-1,3-dioxan-5-yl)heptenoate, as a colourless oil which crystallised after long standing at 4° C. to give solid, m.p. 58°–61° C.;

NMR*: 1.62 (2H, m), 1.80 (1H, m), 1.94 (3H, m), 2.25 (2H, m), 2.53 (1H, m), 3.68 (3H, s) 4.02 (1H, dm J=12 Hz), 4.25 (1H, br d J=12 Hz), 5.11 (1H, q J=3 Hz), 5.30 (1H, m), 5.33 (1H, d J=2 Hz), 5.43 (1H, m), 6.70 (1H, s), 6.83 (1H, br d J=7 Hz), 6.94 (1H, td J=7, 1 Hz), 7.19 (2H, m);

m/e=388 (M+).

EXAMPLE 6

A solution of 5(Z)-7-([2,4,5-cis]-4-o-hydroxyphenyl-2-trifluoromethyl-1,3-dioxan-5-yl)heptenoic acid (374 mg.) in methanol (10 ml.) was treated with 1M sodium hydroxide solution (1.0 ml.) and the mixture stirred for 2 hours. The solvent was evaporated. The residual oil was suspended in toluene and the solvent evaporated. This procedure was repeated twice. The residue was triturated with hexane to give sodium 5(Z)-7-([2,4,5-cis]-4-o-hydroxyphenyl-2-trifluoromethyl-1,3-dioxan-5-yl)heptenoate, as a hygroscopic solid (395 mg), m.p. 88°–93° C.;

calculated for $C_{18}H_{20}F_3O_5Na$, $0.25H_2O$: C, 53.9; H, 5.1%; found: C, 53.9; H, 5.4%.

EXAMPLE 7

A solution of 5(Z)-7-([2,4,5-cis]-4-o-hydroxyphenyl-2-trifluoromethyl-1,3-dioxan-5-yl)-heptenoic acid (374 mg.) in methanol (10 ml.) was treated with 1M sodium hydroxide solution (2.0 ml.) and the mixture stirred for 2 hours. The solvent was evaporated and the residual oil dried by repeated azeotropic evaporation with toluene. The residue was triturated with hexane to give disodium 5(Z)-7-([2,4,5-cis]-4-o-hydroxyphenyl-2-trifluoromethyl-1,3-dioxan-5-yl)heptenoate, as a hygroscopic solid (420 mg.), m.p. 130°–134° C.;

calculated for $C_{18}H_{19}F_3O_5Na_2$, $0.5\ H_2O$: C, 50.6; H, 4.7%; found: C, 50.6; H, 4.8%.

EXAMPLE 8

A solution of 5(Z)-7-([2,4,5-cis]-4-o-hydroxyphenyl-2-trifluoromethyl-1,3-dioxan-5-yl)heptenoic acid (374 mg.) in ether (5.0 ml.) was treated with piperidine (85 mg.) and the mixture stirred for 2 hours. The ether was removed by decantation and the residual oil was crystallised from ethyl acetate/hexane (3:1 v/v) to give the piperidine salt of 5(Z)-7-([2,4,5-cis]-4-o-hydroxyphenyl-2-trifluoromethyl-1,3-dioxan-5-yl)heptenoic acid (368 mg.), m.p. 117°–123° C.;

NMR (200 MHz): 1.65 (11H, m), 2.15 (4H, m), 3.02 (4H, t J=5 Hz), 4.01 (1H, bd J=12 Hz), 4.26 (1H, d J=12 Hz), 5.10 (1H, q J=3 Hz), 5.28 (1H, bs), 5.46 (2H, m), 6.80 (1H, dd J=7, 1 Hz), 6.89 (1H, td J=7, 1 Hz), 7.04 (2H, br), 7.11 (1H, td J=7, 2 Hz), 7.35 (1H, dd J=7, 1.5 Hz);

calculated for $C_{23}H_{32}F_3NO_5$: C, 60.1; H, 7.0; N, 3.05%; found: C, 60.1; H, 7.2; N, 3.1%.

EXAMPLE 9

The following illustrate representative pharmaceutical dosage forms containing the compound of formula I in racemic or laevorotatory optically active form, or a salt thereof (hereafter compound X) for therapeutic or prophylactic use in humans:

| (a) Tablet I | mg/tablet |
|---|---|
| Compound X | 100 |
| Lactose Ph.Eur. | 182.75 |
| AcDiSol | 12.0 |
| Maize starch paste (5% w/v paste) | 2.25 |
| Magnesium stearate | 3.0 |
| (b) Tablet II | mg/tablet |
| Compound X | 100 |
| Lactose Ph.Eur | 173.75 |
| AcDiSol | 6.0 |
| Maize starch | 15.0 |
| Polyvinylpyrrolidone (5% w/v paste) | 2.25 |
| Magnesium stearate | 3.0 |
| (c) Tablet III | mg/tablet |
| Compound X | 1.0 |
| Lactose Ph.Eur | 93.25 |
| AcDiSol | 4.0 |
| Maize starch paste (5% w/v paste) | 0.75 |
| Magnesium stearate | 1.0 |
| (d) Capsule | mg/capsule |
| Compound X | 10 mg |
| Lactose Ph.Eur. | 488.5 |
| Magnesium stearate | 1.5 |
| (e) Injection I | (50 mg.ml.) |
| Compound X (free acid form) | 5.0% w/v |
| 1 M Sodium hydroxide solution | 15.0% v/v |
| 0.1 M Hydrochloric acid (to adjust pH to 7.6) | |
| Polyethylene glycol 400 | 4.5% w/v |
| Water for injection to 100% | |
| (f) Injection II | (10 mg./ml.) |
| Compound X (free acid form) | 1.0% w/v |
| Sodium phosphate EP | 3.6% w/v |
| 0.1 M Sodium hydroxide solution | 15.0% v/v |
| Water for injection to 100% | |
| (g) Injection III | (1 mg/ml, buf to pH 6) |
| Compound X (free acid form) | 0.1% w/v |
| Sodium phosphate BP | 2.26% w/v |
| Citric acid | 0.38% w/v |
| Polyethylene glycol 400 | 3.5% w/v |
| Water for injection to 100% | |
| (h) Aerosol I | mg/ml |
| Compound X | 10.0 |
| Sorbitan trioleate | 13.5 |
| Trichlorofluoromethane | 910.0 |
| Dichlorodifluoromethane | 490.0 |
| (i) Aerosol II | mg./ml |
| Compound X | 0.2 |
| Sorbitan trioleate | 0.27 |
| Trichlorofluoromethane | 70.0 |
| Dichlorodifluoromethane | 280.0 |
| Dichlorotetrafluoroethane | 1094.0 |
| (j) Aerosol III | mg./ml |
| Compound X | 2.5 |
| Sorbitan trioleate | 3.38 |
| Trichlorofluoromethane | 67.5 |
| Dichlorodifluoromethane | 1086.0 |
| Dichlorotetrafluoroethane | 191.6 |
| (k) Aerosol IV | mg./ml. |
| Compound X | 2.5 |
| Soya lecithin | 2.7 |
| Trichlorofluoromethane | 67.5 |
| Dichlorodifluoromethane | 1086.0 |
| Dichlorotetrafluoroethane | 191.6 |

Note

The above compositions may be obtained by conventional procedures well known in the pharmaceutical art. The tablet compositions (a)–(c) may be enteric coated by conventional means, for example to provide a coating of cellulose acetate phthalate. The aerosol compositions (h)–(k) may be used in conjunction with standard, metered dose aerosol dispensers, and the suspending agents sorbitan trioleate and soya lecithin may be replaced by an alternative suspending agent such as sorbitan monooleate, sorbitan sesquioleate, polysorbate 80, polyglycerol oleate or oleic acid.

Scheme 1
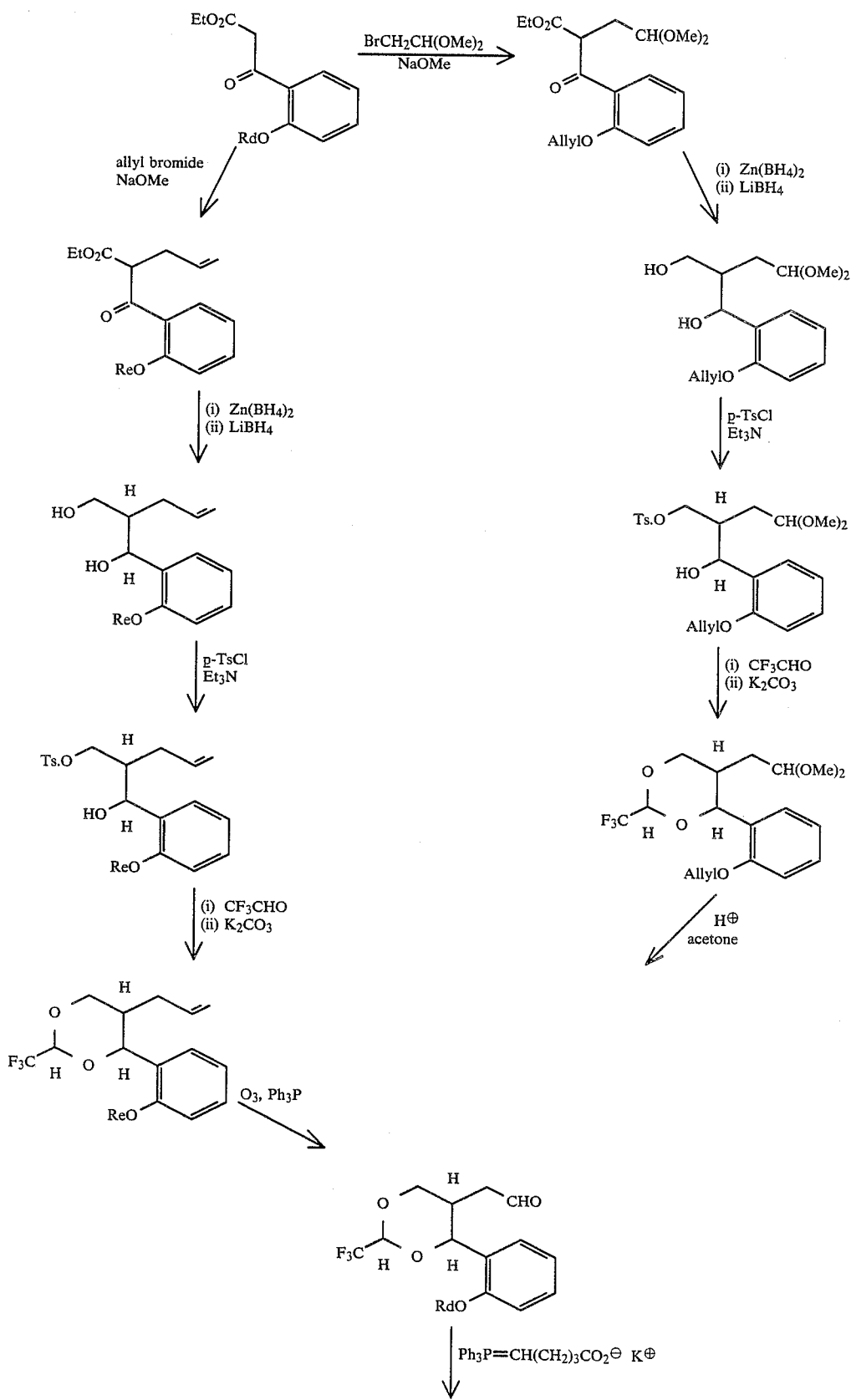

Scheme 1
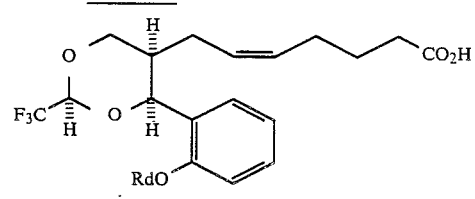
Re = alkyl
benzyl
tetrahydropyran-2-yl
Scheme 2
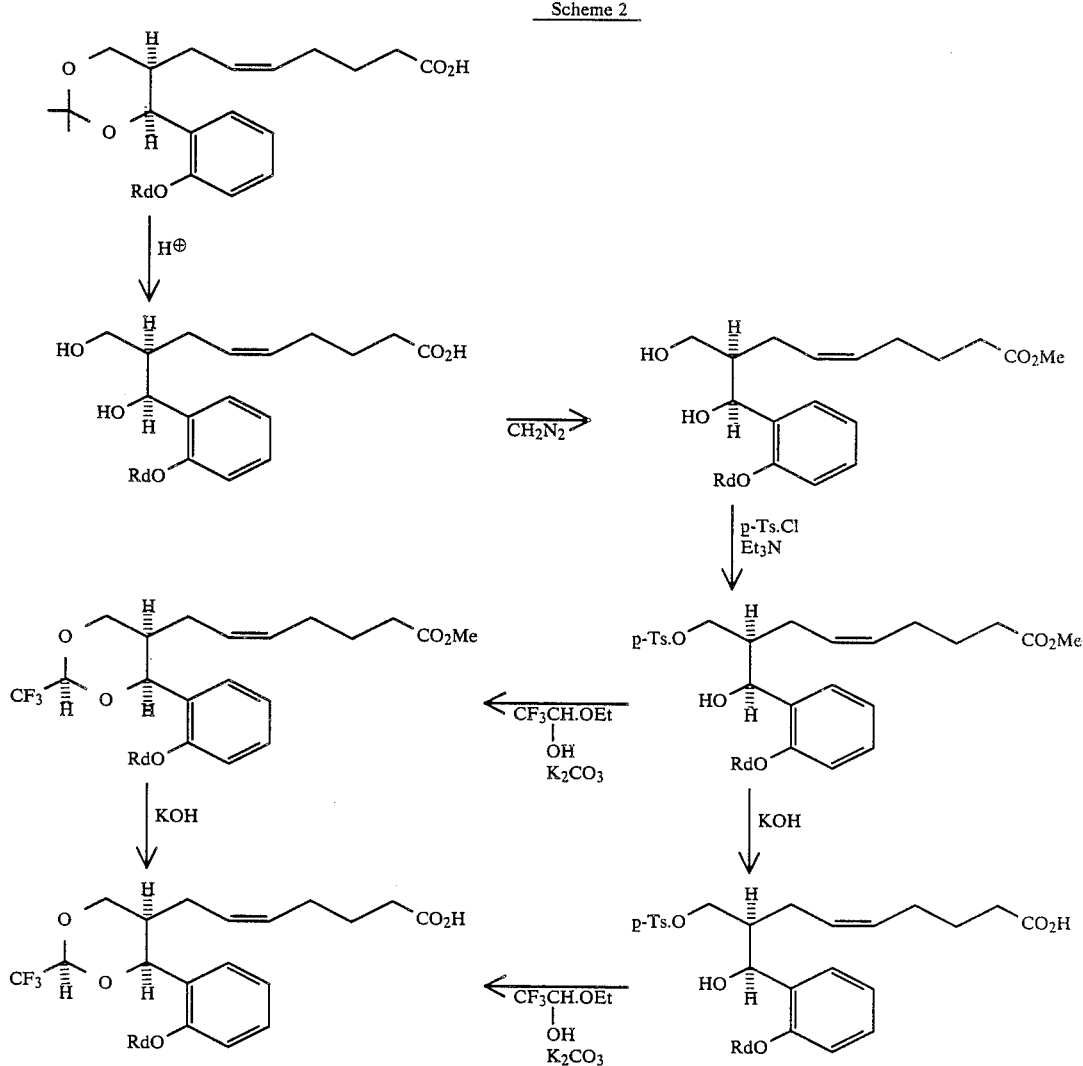
[Rd ≠ alkanoyl or aroyl]
Chemical Formulae (Description)
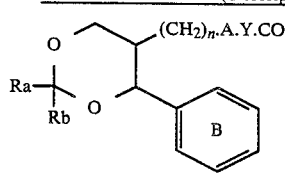  B
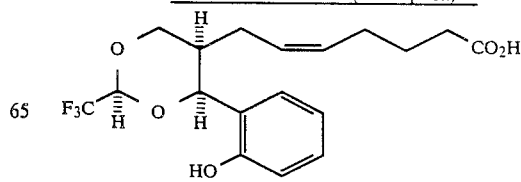  I -continued
Chemical Formulae (Description)

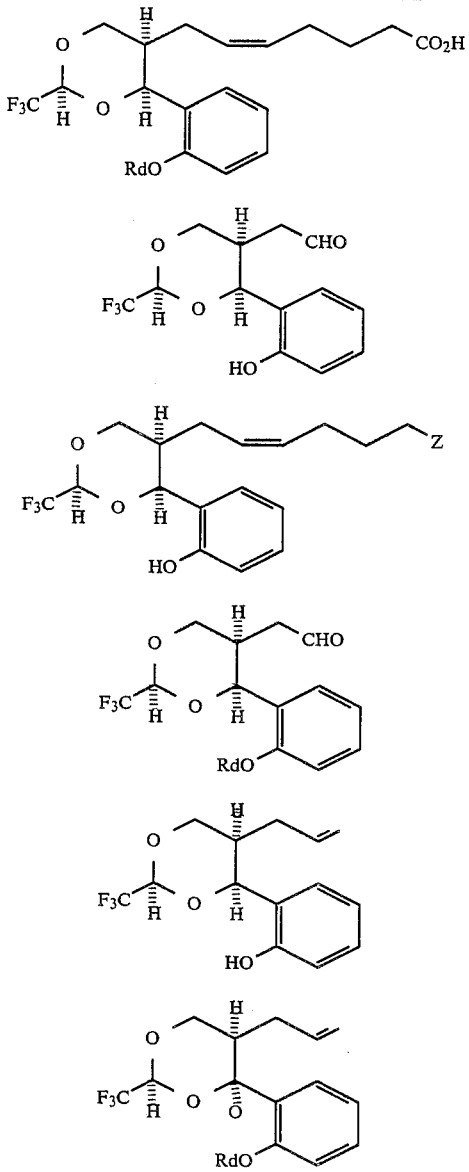

What is claimed is:

1. The compound 5(Z)-7-([2,4,5-cis]-4-o-hydroxyphenyl-2-trifluoromethyl-1,3-dioxan-5-yl)heptenoic acid of the formula

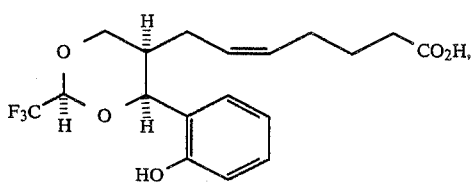

in racemic or laevorotatory optically active form; or a salt thereof.

2. The laevorotatory optically active form of the compound 5(Z)-7-([2,4,5-cis]-4-o-hydroxyphenyl-2-trifluoromethyl-1,3-dioxan-5-yl)heptenoic acid of

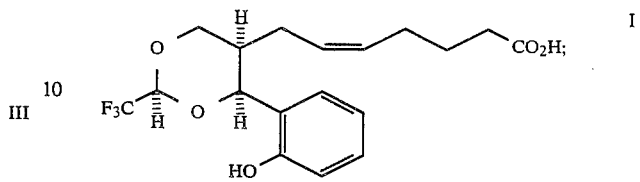

or a salt thereof.

3. A salt as claimed in claim 1 or 2 which is selected from lithium, sodium, calcium, barium, aluminium, ammonium, morpholine, piperidine, ephedrine and optically active alpha-methylbenzylamine salts.

4. A salt as claimed in claim 1 or 2 which is a salt with a base affording a physiologically acceptable cation.

5. A salt as claimed in claim 4 which is selected from sodium, potassium, magnesium, calcium, ammonium, morpholine, piperidine and triethanolamine salts.

6. A method of antagonising one or more of the actions of thromboxane $A_2$ in a warm blooded animal requiring such treatment which comprises administering to said animal an effective amount of the compound 5(Z)-7-([2,4,5-cis]-4-o-hydroxyphenyl-2-trifluoromethyl-1,3-dioxan-5-yl)heptenoic acid of the formula I

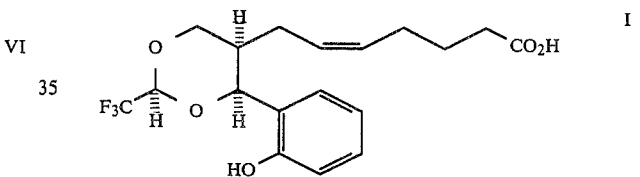

in racemic or laevorotatory optically active form, or a salt thereof with a base affording a pharmaceutically acceptable cation.

7. A pharmaceutical composition suitable for use in antagonizing an action of thromboxane $A_2$ comprising an effective amount of the compound 5(Z)-7-([2,4,5-cis]-4-o-hydroxyphenyl-2-trifluoromethyl-1,3-dioxan-5-yl)heptenoic acid of the formula

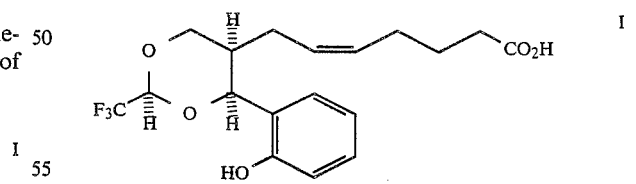

in racemic or laevorotatory optically active form, or a salt thereof with a base affording a physiologically acceptable cation; together with a pharmaceutically acceptable diluent or carrier.

* * * * *